United States Patent
Nobusawa et al.

(10) Patent No.: US 11,408,842 B2
(45) Date of Patent: Aug. 9, 2022

(54) METHOD AND SYSTEM FOR DETECTING SUBSTANCE OF INTEREST IN SOLUTION

(71) Applicant: Osaka University, Osaka (JP)

(72) Inventors: Kazuyuki Nobusawa, Osaka (JP); Ichiro Yamashita, Osaka (JP)

(73) Assignee: Osaka University, Osaka (JP)

( * ) Notice: Subject to any disclaimer, the term of this patent is extended or adjusted under 35 U.S.C. 154(b) by 282 days.

(21) Appl. No.: 16/635,363

(22) PCT Filed: Jul. 5, 2018

(86) PCT No.: PCT/JP2018/025444
§ 371 (c)(1),
(2) Date: Jan. 30, 2020

(87) PCT Pub. No.: WO2019/026517
PCT Pub. Date: Feb. 7, 2019

(65) Prior Publication Data
US 2021/0088461 A1 Mar. 25, 2021

(30) Foreign Application Priority Data
Jul. 31, 2017 (JP) .............................. JP2017-148002

(51) Int. Cl.
*G01N 27/02* (2006.01)
*C12Q 1/686* (2018.01)

(52) U.S. Cl.
CPC .............. *G01N 27/02* (2013.01); *C12Q 1/686* (2013.01)

(58) Field of Classification Search
CPC ................................ C12Q 1/686; G01N 27/02
See application file for complete search history.

(56) References Cited

U.S. PATENT DOCUMENTS

2009/0136933 A1   5/2009  Sakamoto
2012/0285829 A1  11/2012  Mount et al.
(Continued)

FOREIGN PATENT DOCUMENTS

JP   2002-531100 A   9/2002
JP   2004-257993 A   9/2004
(Continued)

OTHER PUBLICATIONS

Aydemir et al., "A Label-Free, Sensitive, Real-Time, Semiquantitative Electrochemical Measurement Method for DNA Polymerase Amplification (ePCR)" Anal. Chem., 2015, 87, 5189-5197.
(Continued)

*Primary Examiner* — Natalie Huls
*Assistant Examiner* — Cynthia L Davis
(74) *Attorney, Agent, or Firm* — Knobbe, Martens, Olson & Bear, LLP

(57) ABSTRACT

The objective of the present invention is to provide a versatile method that makes highly sensitive detection of nucleic acid, and the like, possible even if a solution has a high salt concentration. This objective has been achieved through a method for detecting a target substance in a solution through EIS impedance measurement, wherein the solution includes at least the target substance, an impedance observation substance A, and a substance B for causing the charge mobility of the impedance observation substance to vary, and the substance B for causing the charge mobility to vary has a property of being taken into the target substance.

9 Claims, 4 Drawing Sheets

(56) References Cited

U.S. PATENT DOCUMENTS

| | | | | |
|---|---|---|---|---|
| 2014/0045190 A1* | 2/2014 | Hsing | ............... | C12Q 1/6825 435/6.12 |
| 2015/0148257 A1* | 5/2015 | Schulze | ............... | G01N 27/02 506/12 |

FOREIGN PATENT DOCUMENTS

| | | |
|---|---|---|
| JP | 2013-513790 A | 4/2013 |
| JP | 2015-503095 A | 1/2015 |
| WO | WO 2000/032813 A1 | 6/2000 |
| WO | WO 2007/066479 A1 | 6/2007 |
| WO | WO 2011/069997 A2 | 6/2011 |
| WO | WO 2018/047771 A1 | 3/2018 |

OTHER PUBLICATIONS

Defever et al., "Real-Time Elecrochemical PCR with a DNA Intercalating Redox Probe", Anal. Chem., 2011, 83, 1815-1821.

Gebala et al., "Label-Free Detection of DNA Hybridization in Presence of Intercalators Using Electrochemical Impedance Spectroscopy", Electroanalysis, 2009, vol. 21, No. 3-5, 325-331.

Gebala et al., "Understanding properties of electrified interfaces as a prerequisite for label-free DNA hybridization detection", Phys. Chem. Chem. Phys., 2012, vol. 14, 14933-14942.

Hodko et al., "Detection of Pathogens Using On-Chip Electrochemical Analysis of PCR Amplified DNA Molecules", Proc. SPIE, 2001, 4265, 65-74.

Kelley et al., "Single-base micmatch detection based on charge transduction through DNA", Nucleic Acids Research, 1999, vol. 27, No. 24, 4830-4837.

Shervedani et al., "A modification free hybridization biosensor for detection of DNA sequence based on Zr (IV) ion glue mediated the adsorption on Au-MFA SAM electrode", Sensors and Actuators B, 2011, vol. 160, 145-153.

Singhal et al., "Impedimetric genosensor for detection of hepatitis C virus (HCVI) DNA using viral probe on methylene blue doped silica nanoparticles", International Journal of Biological Macromolecules, Jan. 23, 2017, vol. 98, 84-93.

Veigas et. al., "Field Effect Sensors for Nucleic Acid Detection: Recent Advances and Future Perspectives", Sensors, 2015, 15, 15, pp. 10380-10398.

Nobusawa et al., "A new type of DNA detection using intercalator via electrochemical impedance spectroscopy", Novel Electrochemical Detection of Nucleic Acid by EIS Using Intercalator Molecule, 2017.

* cited by examiner

METHOD AND SYSTEM FOR DETECTING SUBSTANCE OF INTEREST IN SOLUTION

TECHNICAL FIELD

The present invention relates to a method for detecting a target substance existing in a solution and a system for detecting the same, in particular, to a method for detecting a target substance, when a nucleic acid amplified by the polymerase chain reaction (PCR) method is the target substance.

BACKGROUND ART

Conventionally, a technique for examining presence or absence of a nucleic acid having a specific base sequence has been used, for example, in diagnosis of a genetic disease, examination of contamination of food by bacteria and viruses, etc., examination of infection of a human body by bacteria and viruses, etc.

In order to improve detection sensitivity, the nucleic acid was amplified by the PCR method, and the detection of the nucleic acid was performed using an optical method using a fluorescent substance.

This optical method has a problem that the method necessitates an optical detection system, such as a light source or a lens, etc., and this renders the method expensive and difficult to miniaturize. A detection method using a field effect transistor (FET) (hereinafter referred to as FET) instead of the optical means has been proposed (Non-Patent Document 1).

Since the solution used in the PCR method has a high salt concentration and a small electrostatic shielding distance, the electric sensitivity is low. Therefore, a technique for greatly improving the sensitivity has been in a great demand. Detection by the electrochemical impedance spectroscopy (EIS) method has also been proposed, but has been poor in versatility because it is necessary to dispose a specific probe on a working electrode for each target substance to be detected (Patent Document 1).

Patent Document 1: Japanese Unexamined Patent Application (Translation of PCT Application), Publication No. 2015-503095

Non-Patent Document 1: B. Veigas et. al., Sensors, 2015, 15, 15, pp. 10380-10398.

SUMMARY OF THE INVENTION

Problems to be Solved by the Invention

An object of the present invention is provision of a method which can be used for various purposes and which can detect a nucleic acid, etc. in a solution with high sensitivity, even when the solution is in a high salt concentration.

Means for Solving the Problems

The object of the present invention can be achieved by the following embodiments.
(1) A method for detecting a target substance existing in a solution by measuring impedance by an EIS method, in which the solution includes at least the target substance, an impedance observation substance A and an impedance-varying substance B that varies charge transfer characteristics of the impedance observation substance A, and the impedance-varying substance B has a property of being incorporated into the target substance.
(2) The method for detecting a target substance as described in (1) above, in which a substance C having affinity with the impedance-varying substance B is disposed on a working electrode in the EIS method.
(3) The method for detecting a target substance as described in (1) or (2) above, in which the target substance is a nucleic acid.
(4) The method for detecting a target substance as described in any one of (1) to (3) above, in which the method comprises amplifying the target substance.
(5) A system for detecting a target substance existing in a solution, the system having an impedance observation substance A, an impedance-varying substance B that varies charge transfer characteristics of the impedance observation substance A, and a working electrode.

Effects of the Invention

According to the present invention, nucleic acids, etc. can be detected with high sensitivity even at a high salt concentration.

DETAILED DESCRIPTION OF THE PREFERRED EMBODIMENT

Figure 1:
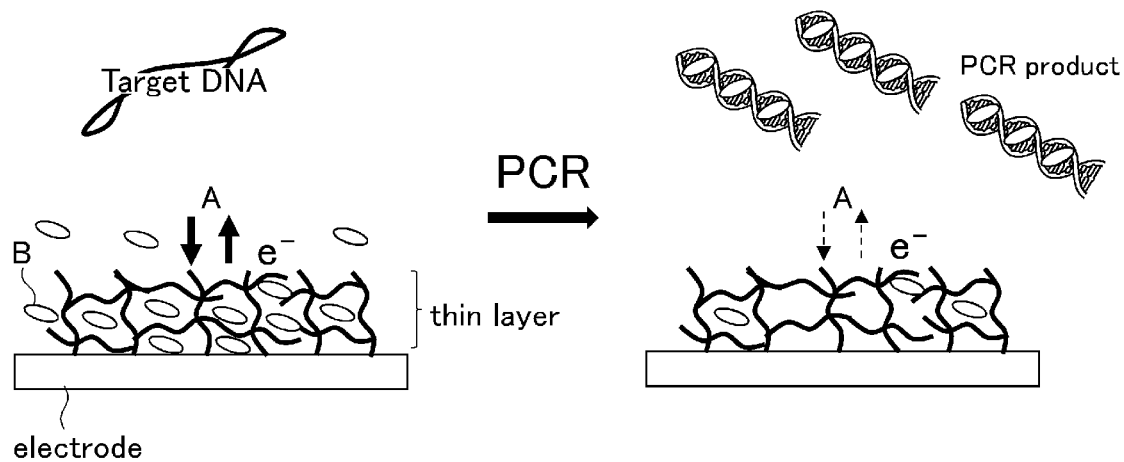
FIG. 1 is a diagram showing an effect-achieving mechanism when the present invention is applied to a PCR method.
Figure 2:
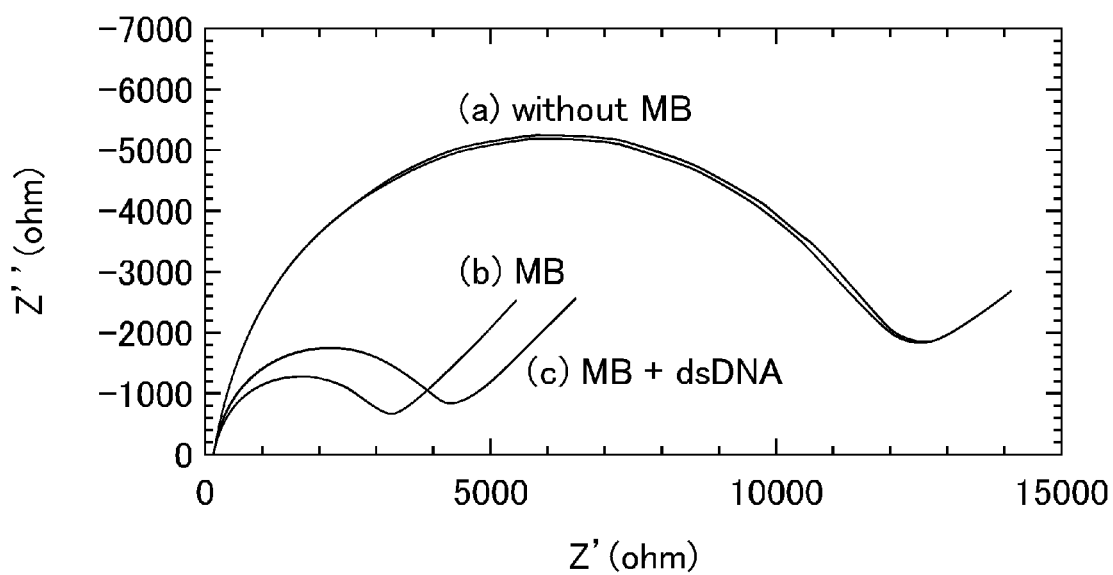
FIG. 2 is a drawing showing variation in impedance of the present invention.
Figure 3:
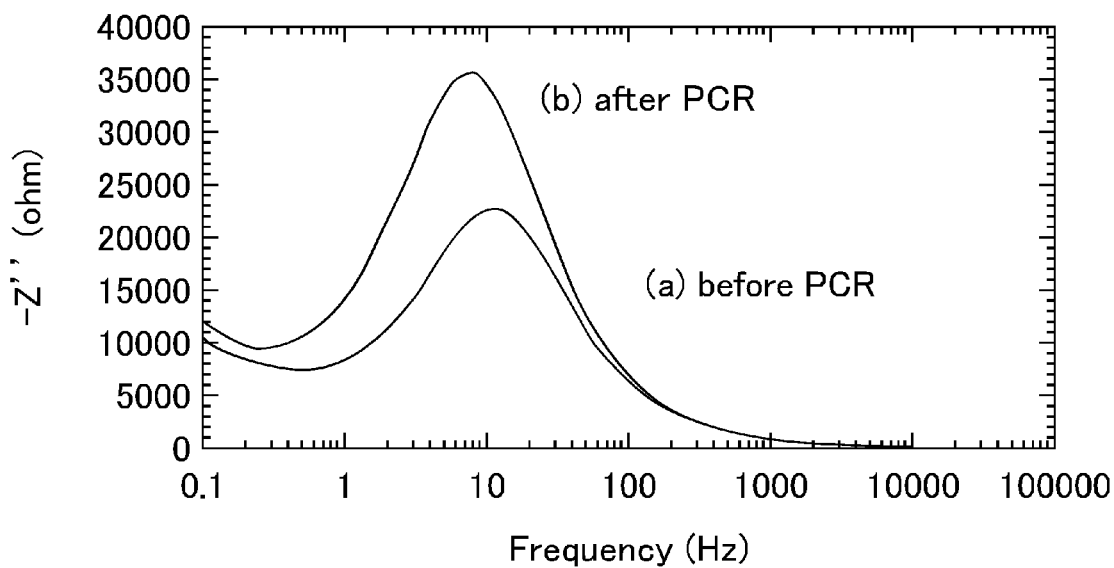
FIG. 3 is a drawing showing data when the present invention is actually applied to the PCR method.

Below, embodiments of the present invention are described in detail.

Detection Method of the Present Invention

The detection method of the present invention is a method of detecting a target substance existing in a solution by measuring impedance by an EIS method, characterized in that the solution includes at least the target substance, an impedance observation substance A and an impedance-varying substance B that varies the charge transfer characteristics of the impedance observation substance A, and the impedance-varying substance B has a property of being incorporated into the target substance.

In the present invention, the target substance to be detected exists in a solution, in particular in an aqueous solution, in which an impedance observation substance A and a substance B that varies the charge transfer characteristics of the impedance observation substance A exist and this substance B, hereinafter referred to as impedance-varying substance B, has a property of being incorporated into the target substance.

For example, as the target substance increases from its initial value, the originally existing impedance-varying substance B decreases because of being incorporated into the target substance and this varies the charge transfer characteristics of the impedance observation substance A. The variation can be either an increase or a decrease in the charge transfer characteristic. In the present invention, an increase in the target substance can be detected by detecting this variation in the charge transfer characteristics in a form of an impedance-response.

<<Target Substance>>

The present invention can be suitably applied for compounds having a nucleic acid or a nucleic acid structure in the molecule. The present invention is particularly suitable for monitoring an increase in double-stranded deoxyribonucleic acid (DNA), which is an amplified product of a nucleic acid by the PCR method. In the present invention, for example, if the initial value of a double-stranded DNA, which is a target substance in PCR-amplification, is 1 ng/ml, the double-stranded DNA can be detected with high sensitivity.

<<Impedance Observation Substance A>>

The present impedance observation substance A expresses a charge with respect to a working electrode, and variation in a degree of the transfer in the solution is perceived as variation in the impedance with respect to the working electrode. It is preferable for the impedance observation substance A not to interact with a substance other than the impedance-varying substance B, which is described below, such as the target substance or a duplicate thereof. Even if it does, interaction is preferably extremely weak. Specifically, a metal complex that forms a redox electrolyte, such as ferricyanide ions, ferrocyanide ions, ferrocene, or the like can be mentioned. In the present invention, it is preferable for the concentration of impedance observation substance A to be 0.1 mM to 10 mM.

<<Impedance-Varying Substance B>>

The impedance-varying substance B of the present invention refers to a substance which generates an action of increasing or decreasing charge transfer characteristics of the impedance observation substance A, when the impedance-varying substance B exists on the electrode interface in the solution, and thus exists in a near field of the impedance observation substance A. Either of the substance which generates an action of increasing or the substance which generates an action of decreasing can be used. It is preferable to increase in terms of sensitivity.

The inventive impedance-varying substance B has a property of being incorporated into the target substance. Here, being incorporated into the target substance means that the target substance and the impedance-varying substance B have chemical or physical interaction, so that the effect on the impedance observation substance A is reduced. For example, compounds that selectively bind within the helical structure of double-stranded DNA, so-called intercalated compounds, are included.

As the amount of a target substance in the solution increases, the impedance-varying substance B interacts with the target substance, and the interaction with the impedance observation substance A decreases. This causes the impedance to vary. The impedance-varying substance B not only affects the impedance observation substance A through its mere approaching effect, but may also cause redox action with the impedance observation substance A, resulting in variation in the charge transfer characteristics.

The impedance-varying substance B may be a fluorescent compound so that it can be used not only for electrochemical detection but also for optical detection. Specifically, compounds having a redox action such as methylene blue, Nile blue, anthraquinone derivatives, naphthalene derivatives, metal ammine complexes and metal complexes containing bipyridine derivatives, phenanthroline derivatives, dipyridophenazine derivatives, or the like as an organic ligand are preferably used. In the present invention, the concentration of an impedance-varying substance B is preferably 0.01 µM (micromolar) to 100 µM. When the reaction progress of the PCR method is simulated, the initial concentration is preferably 0.1 µM to 10 µM.

<<EIS Method>>

The present invention includes using the EIS method for electrical detection, and the detection is performed using, for example, an impedance analyzer. Variation in the charge transfer characteristics of an impedance observation substance A in a solution is expressed in the form of variation in impedance response, the variation being caused on the electrode interface or in the solution due to application of an electric field. Examples of the impedance response include a resistance component (a real number component), a reactance component (an imaginary number component), an impedance absolute value, a phase difference, or a solution resistance, a charge transfer resistance (Rct), Warburg impedance, and an electric double layer capacity derived from the Nyquist plot of an EIS spectrum. In particular, the diameter of a semicircular Nyquist plot of an EIS spectrum is almost equal to the charge transfer resistance Rct. This is intuitively easy to understand and is often used.

In the working electrode of the present invention, it is preferable to dispose a compound C having an affinity for the impedance-varying substance B, on the surface of the solution-side of the working electrode in order to more strongly express the charge-transfer variation of the impedance-varying substance B. This compound C having affinity is disposed so as to modify the electrode surface, and preferably exists, for example, as a thin film layer. When the impedance-varying substance B adopts a structure that allows the impedance-varying substance B to remain in the thin film layer of the compound C, change in the amount of the impedance-varying substance B existing in the thin film layer results in variation in the film resistance as well. This variation can be detected as a rapid change in impedance. It should be noted that not only when the impedance-varying substance B remains in a thin film layer but also when the impedance-varying substance B passes through the thin film layer and reaches the electrode, the variation in the amount can be detected as a rapid change in impedance.

In the present embodiment, the DC voltage applied to the electrodes is generally in the range of −1 to 1 V (volt). When a redox species is used in the measurement, an open circuit potential or a formula potential of the redox species is usually used. The alternating current (AC) voltage applied to the electrodes is not particularly limited, is usually in the range of 1 mV (millivolt) to 1 V, and preferably in the range of 1 to 100 mV in respect of sensitivity. When a redox species is used in the system, both oxidized and reduced species exist, whereby an amplitude of less than 100 mV is usually used. More preferably, the amplitude of AC voltage applied across the electrodes is between about 1 mV and 10 mV.

The compound C having affinity is preferably a compound having weak interaction with components of a PCR-reaction solution, amplifying components, living body derived materials, or the like, and examples thereof include polymers and SAM membranes. On the structural surface, functional groups, such as a hydroxyl group, ether groups, aldehyde groups, carbonyl groups, carboxyl groups, nitro groups, phosphate groups, sulfonate groups, and the like, are disposed. In the case of polymer materials, functional groups are disposed on the main chain or the side chain, or on both of them. Specific examples include polyvinyl alcohols, polyethylene glycol, polyesters, polyacrylic acid, polyacrylamide, polysaccharides, and the like.

Known methods can be applied as a method of disposing the substance C on the electrode. Substance C can also be formed on the electrode by applying electrolytic polymerization, photopolymerization, thermal polymerization, radical polymerization, or the like, using known techniques. The thin film layer is desirably a material having a porous structure through which the substance A can enter and exit, and on or from which the substance B can be adsorbed or desorbed, respectively. The thickness thereof is preferably 0.001 to 10 μm.

With regard to the working electrode of the present invention, the material is not particularly limited as long as the electrode is for electrochemical measurement, but when the compound C is disposed on the surface of the electrode, the electrode is preferably a carbon electrode composed of graphite, carbon nanotubes, carbon black, or the like; a gold electrode; a conductive oxide electrode, such as indium tin oxide (ITO); or the like. In the present embodiment, it is preferable to measure between at least two electrodes, e.g., between a working electrode and any one of the reference electrode and the counter electrode, and the frequency between the electrodes is preferably 0.1 MHz (megahertz) to 1 MHz.

<<Other Additives>>

In the case of detecting, for example, a progress monitor in the PCR method, the inventive solution containing a target substance includes materials used in conventional kits, such as primers, DNA polymerases, targeted DNA, buffering electrolytes, and the like.

In the following Examples, embodiments of the present invention are described, but the present invention is not limited thereto.

EXAMPLES

Example 1

As a thin film layer made of a compound C having affinity with methylene blue (hereinafter sometimes referred to as MB) used as the impedance-varying substance B, a thin film layer containing polyvinyl alcohol was formed on a carbon electrode as a working electrode, and the carbon electrode was disposed in a test aqueous solution. The test aqueous solution was prepared so that the final concentrations of tris buffer, $MgCl_2$ (magnesium chloride), KCl (potassium chloride), and ferricyanide ions-ferrocyanide ions as the impedance observation substance A were 10 mM (millimolar), 1.5 mM, 50 mM, and 1 mM-1 mM, respectively. The EIS measurement was carried out by a three-electrode method in which a working electrode, an Ag/AgCl (silver/silver chloride) reference electrode, and a platinum wire counter electrode were disposed in the aqueous solution.

The EIS measurement of the test aqueous solution was performed at room temperature, and the impedance was measured as an initial value. The measurement conditions were as follows: the DC voltage was an open circuit potential, the AC voltage was 5 mV, the frequency was 100 k to 0.1 Hz, and as the measuring instrument, an impedance analyzer was used. At this time, the Rct derived from the Nyquist plot of the EIS spectrum was 11.8 kΩ(kilo ohms).

Subsequently, 1 μM of methylene blue (MB) was added as the impedance-varying substance B, the solution was stirred sufficiently so that the test aqueous solution for the impedance observation substance A was homogeneous, and then the Rct was measured. The MB concentration was about 1/1,000 of the ferricyanide ion-ferrocyanide ion concentration, but the Rct significantly decreased from 11.6 kΩ to 3 kΩ, namely exhibited a decrease by 8.6 kΩ. This indicated that MB greatly increased the charge transfer characteristics of the ferricyanide ion-ferrocyanide ion.

To this, 1 μM of 40 bp (base pair) double-stranded DNA (dsDNA) was added as a substitute for the PCR-amplified product. As a result, the Rct increased by 1.08 kΩ, i.e., by about 36%. This indicated that the MB was intercalated, in other words, incorporated into the double-stranded DNA, and the charge transfer characteristic effect decreased.

Thus, the charge transfer characteristics of the ferricyanide ion-ferrocyanide ion of the impedance observation substance A is enhanced by MB as the impedance-varying substance B, and further the double-stranded DNA incorporates the MB and varies the charge transfer characteristics thereof, and thereby the double-stranded DNA can be detected by the EIS measurement.

Example 2

A similar test was conducted using a ruthenium complex having bipyridine and dipyridophenazine as ligands, i.e., bis(2,2'-bipyridine) dipyrido[3,2-a:2',3'-c]phenazine ruthenium(II) (hereinafter referred to as $Ru(bpy)_2DPPZ$ complex), as the impedance-varying substance B, instead of the above-mentioned methylene blue. The contribution to the variation in the Rct was further enhanced compared to that by methylene blue, and the increase in Rct by 1 μM double-stranded DNA of 40 bp was 84%.

Thus, the charge transfer characteristics of the ferricyanide ion-ferrocyanide ion of the impedance observation substance A is enhanced by the $Ru(bpy)_2DPPZ$ complex as the impedance-varying substance B, and further the double-stranded DNA incorporates the $Ru(bpy)_2DPPZ$ complex and this varies the charge transfer characteristics thereof, and thereby the double-stranded DNA can be detected by the EIS measurement.

Example 3

Under the test aqueous solution conditions used in Example 2, enzymes, dNTPs, primers and DNA template, etc. required for the PCR were added to perform the PCR, and the solutions before and after the PCR were subjected to two-electrode method EIS measurement using the same working electrode and platinum wire counter electrode as in Example 2. The PCR was performed using pUC18 as the DNA template, M13M4 as the forward primer, M13Rv as the reverse primer, and using rTaqDNA polymerase, followed by a denaturation step of 95° C. for 2 minutes. Then, 30 cycles of three step temperature settings of 95° C., 55° C., and 72° C. were conducted.

In the board plot of the EIS spectrum, the PCR amplified product increased the maximum of the impedance imaginary number component (−Z") from 22.8 kΩ to 35.8 kΩ after the PCR, in the frequency range of 100 k to 0.1 Hz. In other words, the PCR amplified product increased the imaginary number component by 57%. As the change in the Rct, the Rct increased from 52 kΩ to 80 kΩ, by about 54%. This indicates that the present invention is effective for detecting double-stranded DNA, which is a PCR product.

Example 4

The EIS measurement was conducted during performing temperature cycles of the PCR by using a two-electrode method comprising use of a parallel electrode for the working electrode, ferricyanide ion-ferrocyanide ion as the impedance observation substance A, and a Ru(bpy)$_2$DPPZ complex as the impedance-varying substance B. Mitochondrial DNA at 1 ng/ml was used as the template DNA.

The PCR solution was as described in Table 1: a mixture prepared by adding DNA synthase and a dNTP required for the PCR to tris buffer at 10 mM, MgCl$_2$ at 1.5 mM and KCl at 50 mM, and adding ferricyanide ion-ferrocyanide ion and a Ru(bpy)$_2$DPPZ complex, so as to be 1 mM and at 1 μM, respectively.

Figure 4:
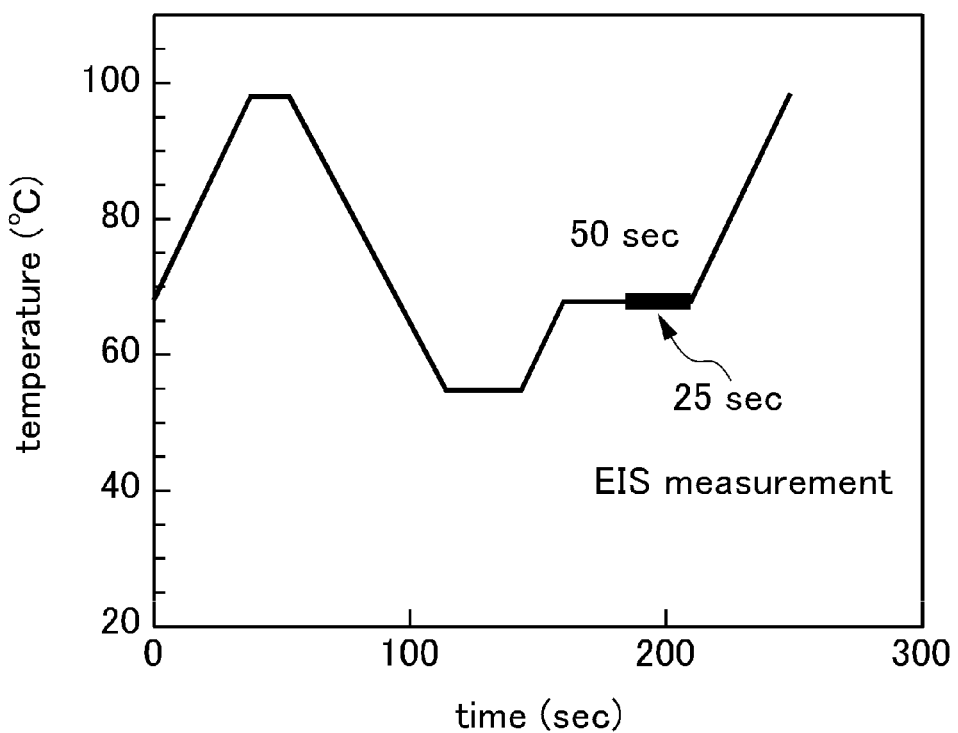
FIG. 4 is a drawing showing temperature setting and EIS measurement timing for one temperature cycle of real time PCR of the present invention.

After the solution was first heated at 98° C. for 2 minutes, the solution was subjected to a temperature cycle of 98° C. for 10 seconds→57° C. for 30 seconds→68° C. for 30 seconds, 10 times, then the holding time of 68° C. was extended to 50 seconds, and the latter half of 25 seconds was used for EIS measurement (FIG. 4). This temperature cycle including the EIS measurement was carried out 30 times (98° C. for 15 seconds→55° C. for 30 seconds→68° C. for 50 seconds). As a comparison, the EIS measurement was performed by exactly the same operation with no DNA template being added.

TABLE 1

| Reagent | Amount | Unit |
|---|---|---|
| Mitochondrial DNA | 1 | ng/mL |
| Forward primer | 0.5 | μM |
| Reverse primer | 0.5 | μM |
| dNTP | 0.4 | mM |
| DNA synthase | 0.02 | unit/μL |
| Tris buffer | 10 | mM |
| KCl | 50 | mM |
| MgCl$_2$ | 1.5 | mM |
| Ru(bpy)$_2$DPPZ | 1 | μM |
| Ferricyanide ion | 1 | mM |
| Ferrocyanide ion | 1 | mM |

Figure 5:
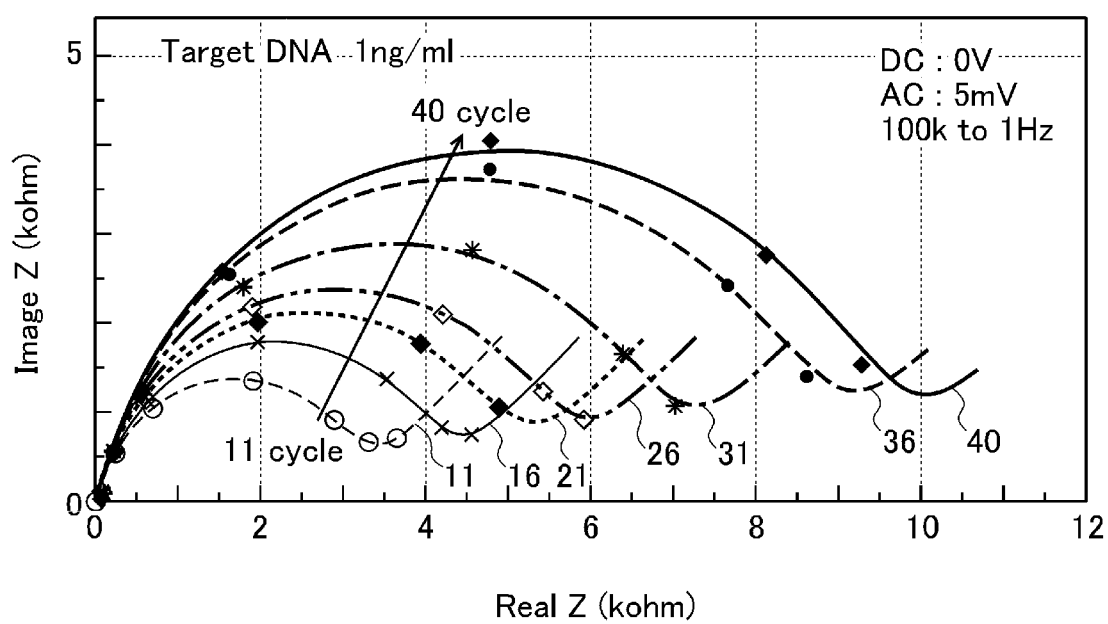
FIG. 5 is an example of a Nyquist plot of the 11th to 40th EIS measurements results of the PCR temperature cycles, when the present invention is applied to the real time PCR method.

FIG. 5 shows typical Nyquist plots of the results of EIS measurements from the 11th to the 40th PCR temperature cycles containing 1 ng/ml of DNA template. At each temperature cycle, the EIS measurements drew typical semicircles, the diameter of which increased with each temperature cycle. It was shown that the Ru(bpy)$_2$DPPZ complex was incorporated into the double-stranded DNA which is a PCR amplification product, and this resulted in an increase in the Rct.

In addition, the rate of increase in the Rct was increasing around the temperature cycle of $25^{th}$ to $30^{th}$ cycles. This indicates that the increase in double-stranded DNA reached maximum in the PCR process and is consistent with the DNA amplification behavior in optical PCR monitoring.

Figure 6:
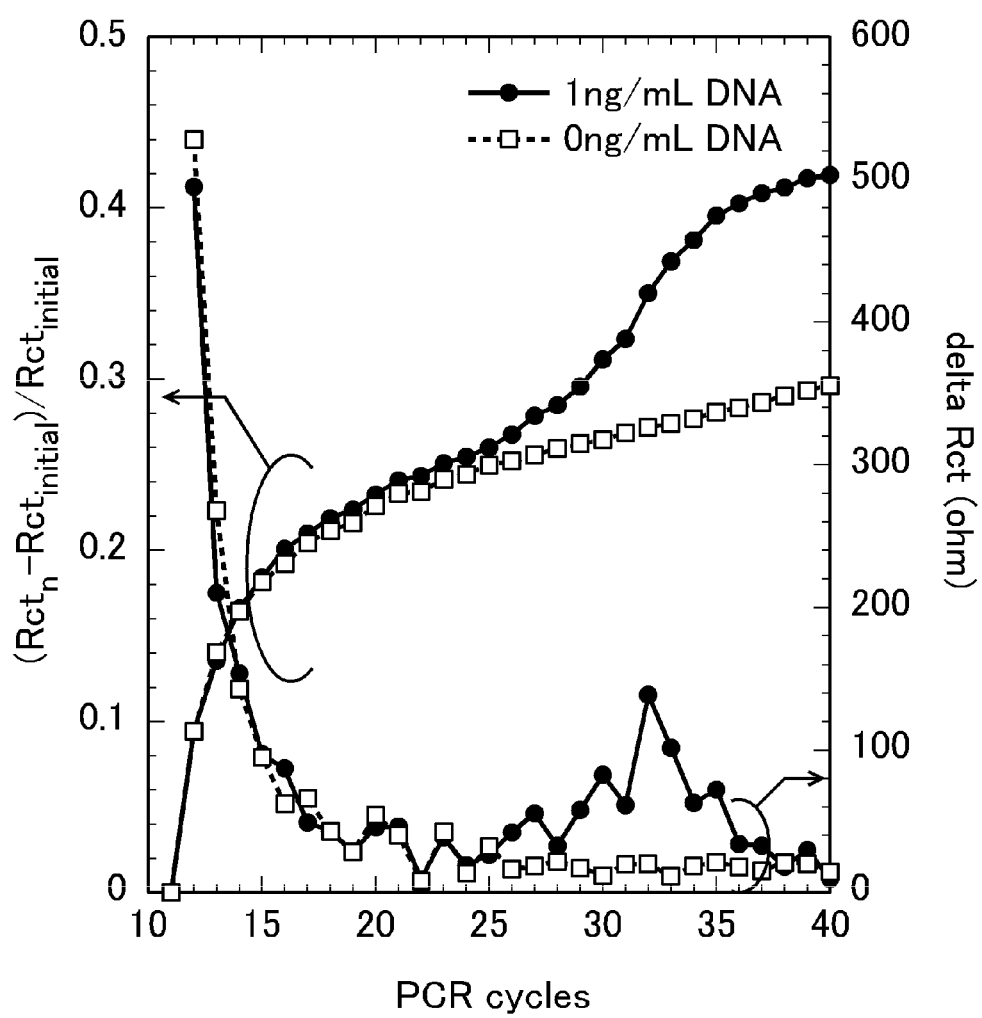
FIG. 6 is a drawing showing change in a charge transfer resistance Rct obtained by calculation from the 11th to 40th EIS results of the PCR temperature cycles, when the present invention is applied to the real time PCR method.

FIG. 6 is a graph of the Measurement Examples obtained by calculating Rcts from the EIS measurements results and the right scale plots the increment (delta Rct) of the Rcts for each temperature cycle. Upon comparing the case including a DNA template (1 ng/mL DNA) with the case including no DNA template (0 ng per mL DNA), in the former, the Rct starts to rapidly increase in the range of 25 to 30 cycles. This indicates that the double-stranded DNA markedly increased from around this range. Note that $(Rct_n - Rct_{initial})/Rct_{initial}$ is a value obtained by dividing (the observed Rct-the initial Rct) by the initial Rct. This graph also shows that the Rct began to increase rapidly in the range of 25 to 30 cycles.

No abrupt change in the Rct was observed in the EIS measurement of the control experiment including no target DNA. This can also be seen by plotting the increment of the Rct for each temperature cycle (the right scale in FIG. 6).

In order to shorten time, in the present Examples, an observation step was skipped for the first 10 temperature cycles, but the number of times a temperature step can be skipped can be appropriately changed. For example, when the template DNA is at a low concentration, the observation step can be skipped up to 15 to 20 times. In addition, it is also possible to appropriately change the setting of the number of total temperature cycles and the setting of the temperature and the holding time in all PCR cycles in accordance with the observation object.

As can be seen from the above Examples, it was indicated that the present invention has the following features: being effective for detecting double-stranded DNA, which is a PCR product; being resistant to temperature cycles at 55 to 98° C.; enabling measurement in a short time, which is difficult by conventional EIS measurement; and enabling PCR progress in real time.

From the above experimental results, it was clarified that the present invention is useful for detecting various types of target substances, such as nucleic acids in solutions, and that the present invention can be applied to real time measurement, so that the present invention also enables quantitative evaluation and also has versatility.

EXPLANATION OF REFERENCE NUMERALS

A: Impedance observation substance A
B: Impedance-varying substance B
e−: Charge

What is claimed is:

1. A method for detecting a target substance existing in a solution, comprising measuring impedance of the solution by an electrochemical impedance spectroscopy (EIS) method,
   wherein the solution comprises:
       at least the target substance, wherein the target substance is not fixed to an electrode,
       an impedance observation substance A, and
       an impedance-varying substance B varying charge transfer characteristics of the impedance observation substance A,
       wherein neither the impedance observation substance A nor the impedance-varying substance B has a nucleic acid sequence structure,
   wherein the impedance observation substance A expresses a charge to a working electrode and does not interact with a substance other than the impedance-varying substance B, and the impedance-varying substance B has a property of being incorporated into the target substance, and
   wherein the solution comprises the target substance intercalated with the impedance-varying substance B.

2. The method for detecting a target substance according to claim 1, wherein a substance C having affinity with the impedance-varying substance B is disposed on the working electrode in the EIS method.

3. The method for detecting a target substance according to claim 1, wherein the target substance is a nucleic acid.

4. The method for detecting a target substance according to claim 1, wherein the solution in which the target substance is detected comprises a deoxyribonucleoside triphosphate (dNTP).

5. The method for detecting a target substance according to claim 1, wherein the impedance-varying substance B is a compound having a redox action.

6. The method for detecting a target substance according to claim 1, wherein the method further comprises amplifying the target substance.

7. The method for detecting a target substance according to claim 1, wherein the detection of the target substance detects reduction in an action of the impedance-varying substance B on the impedance observation substance A.

8. The method for detecting a target substance according to claim 6, wherein amplifying the target substance and measuring impedance are performed in the same solution.

9. The method for detecting a target substance according to claim 5, wherein the compound having a redox action is selected from the group consisting of methylene blue, Nile blue, anthraquinone derivatives, naphthalene derivatives, metal ammine complexes and metal complexes containing bipyridine derivatives, phenanthroline derivatives, or dipyridophenazine derivatives as an organic ligand.

* * * * *

UNITED STATES PATENT AND TRADEMARK OFFICE
CERTIFICATE OF CORRECTION

PATENT NO. : 11,408,842 B2
APPLICATION NO. : 16/635363
DATED : August 9, 2022
INVENTOR(S) : Kazuyuki Nobusawa It is certified that error appears in the above-identified patent and that said Letters Patent is hereby corrected as shown below:

On the Title Page

Page 2, Column 1 (Other Publications), Line 1, delete "Elecrochemical" and insert
-- Electrochemical --.

Page 2, Column 2 (Other Publications), Line 7, delete "micmatch" and insert -- mismatch --.

Signed and Sealed this
Seventeenth Day of January, 2023

Katherine Kelly Vidal
*Director of the United States Patent and Trademark Office*